United States Patent [19]

Smith et al.

[11] Patent Number: 4,665,263
[45] Date of Patent: May 12, 1987

[54] ETHYLENE POLYMERIZATION WITH POLYCHROMIUM CATALYSTS AND RESULTING POLYMER

[75] Inventors: Paul D. Smith; Eric T. Hsieh, both of Bartlesville, Okla.

[73] Assignee: Phillips Petroleum Company, Bartlesville, Okla.

[21] Appl. No.: 842,700

[22] Filed: Mar. 21, 1986

Related U.S. Application Data

[62] Division of Ser. No. 640,062, Aug. 13, 1984, Pat. No. 4,587,227.

[51] Int. Cl.$^4$ ................................................ C07C 2/30
[52] U.S. Cl. ........................................ 585/520; 526/96; 526/97; 526/126; 526/129; 526/166; 526/170; 585/510; 585/530; 585/511
[58] Field of Search ............... 585/520, 521, 530, 510, 585/511; 526/96, 97, 126, 129, 166, 170

[56] References Cited

U.S. PATENT DOCUMENTS

| | | | |
|---|---|---|---|
| 2,840,508 | 10/1974 | Ballard et al. | 526/126 |
| 3,378,536 | 4/1968 | Walker et al. | 502/154 |
| 3,468,865 | 9/1969 | Santiago | 526/126 |
| 3,763,197 | 10/1973 | Collier et al. | 502/153 |
| 3,879,368 | 4/1975 | Johnson | 502/102 |
| 4,001,195 | 1/1977 | Wyatt | 526/126 |
| 4,018,707 | 4/1977 | Wyatt | 502/154 |
| 4,325,839 | 4/1982 | McDaniel | 502/154 |
| 4,369,295 | 1/1983 | McDaniel | 502/150 |
| 4,587,227 | 5/1986 | Smith et al. | 502/153 |

OTHER PUBLICATIONS

Chem. Abstracts, 89:43695k (1978).
Chem. Abstracts, 92:111529y (1980).

*Primary Examiner*—Asok Pal
*Attorney, Agent, or Firm*—A. L. Robbins

[57] ABSTRACT

Olefin polymerization catalysts are described which are based on solid inorganic oxides (such as silica) and polychromium complexes (such as octakis($\mu$-trimethylsilylmethyl) tetrachromium(II)). Linear low density ethylene homopolymers with specific short chain branching as well as polymerization processes to make these polymers using the specific catalyst described are also disclosed.

19 Claims, 2 Drawing Figures

ETHYLENE POLYMERIZATION WITH POLYCHROMIUM CATALYSTS AND RESULTING POLYMER

This application is a division of application Ser. No. 640,062 filed Aug. 13, 1984, now U.S. Pat. No. 4,587,227.

This invention relates to polymers made from ethylene. In another aspect, this invention relates to chromium catalysts and in particular to dual valence chromium catalysts. In yet another aspect this invention relates to processes to polymerize olefins using such chromium catalysts as well as to processes to make the catalysts.

BACKGROUND OF THE INVENTION

Low pressure ethylene polymerization and copolymerization is widely practiced commercially. One successful catalyst system for such a polymerization is based on chromium. The basic process is described in U.S. Pat. No. 2,825,721. High density ethylene homopolymers as well as ethylene/1-olefin copolymers of lower density have been commercially produced using chromium catalysts for many years.

The copolymerization of ethylene and other olefins results in the generation of side chains or side groups along the main carbon chain of the polymer. Thus, copolymerization of ethylene and propylene results in methyl side groups while butene-1 or respectively hexene-1, when copolymerized with ethylene over chromium catalysts, results in polymers having ethyl or respectively n-butyl side chains. The number of side chains, their lengths and their distribution in the polymer molecule influence the properties of the polymer. Generally speaking side chains in the polymer tend to disrupt the crystallinity of the polymer and thereby reduce the density.

The price of sufficiently pure 1-olefins has originally caused the use of butene-1 as the major 1-olefin used in the production of modified ethylene polymer resins. Later, when hexene-1 became available at reasonable prices and purities, this olefin was used extensively in the production of such modified ethylene polymers. However, 1-olefins, such as butene and hexene, still are significantly more expensive than ethylene and thereby increase the price of ethylene/1-olefin copolymers produced.

More recently a low pressure polymerization process has been discovered by which a polymer is produced using only ethylene as the monomer and yet resulting in a linear polymer having short side chains. Unlike high pressure (free radical) ethylene polymerization, this process does not cause any significant long chain branching. Such a process for producing linear low density polyethylene using only ethylene as a feedstock is described in U.S. Pat. No. 4,325,839 which issued to Max P. McDaniel. One of the advantages of this new process is that only ethylene and no other olefins are necessary to produce a copolymer with the modifying short side chains.

Although the possibility of making short chain branched, linear ethylene homopolymers using mixed chromium catalysts is an exciting new technology, further development is desirable.

THE INVENTION

It is one object of this invention to provide novel ethylene polymers. In particular, it is an object of this invention to provide such polymers which allow industrial application in areas such as blow molding.

Another object of this invention is to provide a process for polymerizing ethylene into low density linear polymers. A particular object of this invention is to provide such a process in which no olefins of very low molecular weight or only a relatively small amount of such olefins are produced, e.g. oligomers of ethylene.

Another object of this invention is to provide a new olefin polymerization catalyst. A more specific object is to provide such a catalyst which, when employed in ethylene polymerization, produces a polymer which after removal of any solvent or diluent is substantially dry and non-sticky.

Yet a further object of this invention is to provide a process to produce such polymerization catalysts.

In accordance with this invention it now has been found that a novel chromium-based catalyst allows the production of various olefin polymers and particularly linear low density polymers from ethylene alone with desirable properties of the polymer produced and with desirable features for the polymerization process. This new polymerization catalyst is characterized by the incorporation of a specific novel chromium compound to be defined in the following disclosure. This novel chromium compound is not as such herein claimed but is claimed and disclosed in a co-pending patent application.

THE CATALYST

In accordance with a first embodiment of this invention a novel catalyst is provided. This catalyst is characterized by a solid support and a chromium compound.

The novel chromium compound is characterized by the formula $$Cr_n(R)_{2n}$$

wherein
n is an integer of 3 or more, preferably 4–6, most preferably n is 4;
R is a ligand having the formula $$-CH_2-MR^1R^2R^3$$

wherein
M is C, Si, Ge, Sn or Pb, preferably Si;
$R^1$, $R^2$, $R^3$, which can be the same or different, are hydrocarbyl substituents consisting of carbon and hydrogen atoms, preferably having 1 to 12 carbon atoms and usually being selected from the group consisting of alkyl, aryl, alkaryl, aralkyl, alkenyl radicals; alkyl radicals of 1-3 carbons, particularly methyl, being preferred.

Specific examples of compounds of this invention are:

$$Cr_4[CH_2C(CH_3)_3]_8$$

$$Cr_4[CH_2Si(CH_3)_2CH_2CH=CH_2]_8$$

$$Cr_4[CH_2Si(CH_3)_3]_8$$

$$Cr_4[CH_2Si(CH_3)_2CH_2C_6H_5]_8,$$

$$Cr_4[CH_2Si(C_6H_5)_3]_8$$

where $C_6H_5$ is phenyl.

The n chromium atoms of the novel compounds of this invention are connected to each other in a single or double ring structure, preferably as one ring of 4 chromium atoms. The ring structure and the above formula is believed to accurately describe the novel compounds. It should be emphasized, however, that complex chemical bonds are involved in the novel molecules of this invention and the details scientific analysis and description of these compounds are given with the understanding that the invention here involved should not be limited theregy.

BRIEF DESCRIPTION OF DRAWINGS

The presently preferred chromium compound is octakis($\mu$-trimethylsilylmethyl)tetrachromium(II). This compound is schematically shown in FIGS. 1 and 2.

In FIG. 1 the hydrogens of the exterior methyl groups have been left off for clarity.

Each of the silicon atoms (Si1 to Si8) has 3 methyl groups attached to it.

The novel chromium compounds here involved can be made by a process as described in detail in the following. The process, too, does not constitute as such a separate embodiment of this invention. This process, too, is claimed and disclosed in the above-mentioned companion patent application.

PROCESS TO MAKE THE CHROMIUM COMPOUNDS

The process of making these chromium compounds comprises adding a magnesium compound having the formula Y—Mg—R, wherein Y is halogen or R, and preferably a Grignard reagent (Y=halogen) wherein the substituent R is as defined above to a solution of $CrX_2$ in a solvent and recovering the chromium compound produced thereby from said solvent. X is chlorine, bromine or iodine. Instead of the Grignard reagent is is also within the scope of this invention to use a compound $MgR_2$, wherein R has the meaning as defined above.

The preferred Grignard reagent used has the general formula XMgR, wherein R is as defined above.

The preferred $CrX_2$ compound used in this process is $CrCl_2$. Various liquids for suspending the chromium dihalide can be used. It is particularly preferred to use a liquid which increases the solubility of the chromium dihalide in the reaction fluid medium. Thus, a liquid which is a Lewis base is preferred. Ethers can be used. Cyclic ethers such as tetrahydrofuran (THF) are particularly preferred.

The Grignard reagent, or respectively $MgR_2$, is added to the suspension of the chromium halide. It is preferred that the magnesium compound is added in the form of a solution. Ethers are particularly preferred solvents for the magnesium compounds, e.g. the Grignard reagents, here involved. Diethyl ether is the presently preferred solvent for this compounds.

Some of the Grignard reagents here involved are commercially available materials. These products can also be conveniently produced by adding a compound having the formula X—R, wherein X is a halide atom and R has the above-defined meaning, chlorine being preferred for X, to finely divided elemental magnesium, such as magnesium turnings, suspended in a dry diluent such as diethyl ether or THF.

For the production of the novel Cr compounds, it has been found that the order of addition of the reactants is important. It has been found that the Grignard reagent should be added dropwise to a suspension of $CrCl_2$ in the reaction fluid (e.g. THF) to prepare the desired polychromium ring complexes. When $CrCl_2$ is added to the Grignard reagent, the prior art Cr complexes are formed. It is presently believed that the same order of addition is to be employed in the case of $MgR_2$ as the starting material.

The diluents, solvents and reactants used in the process of this invention are preferably employed in ranges as shown in the following table.

TABLE

| | Broad | Specific |
|---|---|---|
| Agent (to substitute —R), preferably YMgR (mole) | 1.8 to 3 | 1.9 to 2.2 |
| Solvent, mL per g Agent | 2 to 10 | 3 to 6 |
| $CrX_2$ (mole) | 1 | 1 |
| Diluent, mL per g $CrX_2$ | 50 to 500 | 75 to 150 |

The above tabulation is based on 1 mole of $CrX_2$; fractions or multiples thereof are of course contemplated, as will be apparent to a person skilled in the art.

The compounds prepared by the reaction step described are recovered by separation techniques including decanting, filtering, washing, drying, particularly vacuum drying. It is presently preferred to extract the product of the reaction step of the inventive process following the solvent removal with hydrocarbon fluids such as alkanes, particularly preferred is n-pentane.

SUPPORTS

The supports on which the new compounds exhibit their catalytic activity are preferably inorganic oxide-containing supports. Particularly preferred are supports selected from the group consisting of silica, silica-alumina, alumina, fluorided alumina, silated alumina, thoria, aluminum phosphate, phosphated silica, phosphated alumina, silica-titania, coprecipitated silica/titania, fluorided silated alumina being presently preferred, and mixtures thereof as well as any one or more of these supports containing chromium, preferaby chromium in an activated stage such as hexavalent chromium.

One particular application of the new compounds and a first variation of this embodiment of this invention is an olefin polymerization catalyst containing two or more different catalytic sites. Particularly the new compounds can be employed in dual valence chromium catalysts. In these applications, the new chromium compounds are contacted with an already active olefin polymerization catalyst. A preferred dual site catalyst is obtained by contacting one or more of the new chromium compounds with an olefin polymerization catalyst comprising catalytically active chromium sites. An example of such application would be to contact the new chromium compounds with an olefin polymerization catalyst containing hexavalent chromium. In accordance with a preferred catalyst of this invention these new chromium compounds are contacted with an activated chromium catalyst, the latter often being referred to as a Phillips catalyst. Such Phillips catalysts are described in, e.g., U.S. Pat. No. 2,825,721, U.S. Pat. No.

3,887,494, U.S. Pat. No. 4,081,407 and U.S. Pat. No. 4,312,967.

The preferred supports used for the production of the catalyst of this invention are characterized by the following physical properties:

| Physical Properties | Physical Characteristics of the Preferred Supports | |
| --- | --- | --- |
|  | Broad | Specific |
| Pore Volume[1], cc/g | 0.4 to 3.5 | 0.8 to 2.5 |
| Surface Area[2], m$^2$/g | 200 to 800 | 250 to 600 |

[1] As determined by mercury intrusion.
[2] As determined by BET/nitrogen sorption The catalysts of this invention are made from the support and the chromium compound as defined. Generally speaking about 0.01 to 2 parts by weight of chromium per 100 parts by weight of support are utilized on the catalyst. Preferably the range for the chromium compound is 0.1 to 1.5 parts by weight of chromium per 100 parts by weight of solid support. As pointed out, the solid support is either an inorganic oxidic support as such or is such a support having additionally incorporated therein chromium catalytic sites, preferably hexavalent activated chromium catalytic sites.

PROCESS TO PRODUCE THE CATALYST

In accordance with a second embodiment of this invention a process to produce the novel catalyst defined above is provided. This process includes contacting the solid support with the chromium compound defined under the usual dry, oxygen-free conditions. This contacting is preferably done by impregnating the support with the compound using a solution of the new compound. Following such an impregnation step, the solvent is removed by such techniques as decanting and vacuum drying. It is not inconceivable that in this process the chromium compound defined above undergoes complexing and/or chemical reactions with the support. Applicants do not wish to be bound by any theory in this area, however.

When a solution of the novel chromium compounds is used to impregnate the support, the chromium compound is utilized in a quantity of 0.05 to 5 parts by weight of Cr per 100 parts by weight of solvent. Suitable solvents for this purpose are n-pentane, n-hexane, cyclohexane, THF and ethanol (anhydrous).

Alternatively, the support and the chromium compound can be separately charged to a polymerization reactor where they react prior to or during admitting of the monomer(s).

THE POLYMERIZATION PROCESS

The catalyst described above can be used for the polymerization of ethylene and other olefins. The catalysts are particularly useful for the polymerization of olefins having 2 to 12, preferably 2 to 8 carbon atoms. A further embodiment of this invention resides in a process to polymerize or copolymerize ethylene using the catalyst defined above. The preferred process uses ethylene as the sole olefinic feedstock.

The polymerization process of this invention can be carried out in gas phase, solution or particle (slurry) form. The presently preferred process is one in which a liquid diluent together with the ethylene and optionally further olefin, particularly up to 10 mole % of 1-olefins having 3 to 12, preferably 4-8, carbon atoms is employed. Examples for such diluents or solvents are paraffins, cycloparaffins or aromatic hydrocarbons, with about 3 to 12 carbon atoms, particularly isobutane, isopentane, cyclohexane and benzene. The preferred diluent or solvent is isobutane.

The polymerization conditions employed are those well known to persons skilled in the art in this area. The conditions are not particularly critical and the specific condition utilized depends largely upon the desired results. Typical ranges for such polymerization conditions are given in the following:

| | |
| --- | --- |
| Temperature | 0 to 450° F. |
| Pressure | 100 to 700 psia |
| (pressure is high enough to maintain the liquid phase under the polymerization temperature conditions) | |
| Polymerization Time | 15 to 180 min. |
| Catalyst Concentration | 0.005 to 0.200 g/l of reactor contents |

The polymer produced by the process of this invention is recovered utilizing also standard techniques. These techniques involve settling, flashing, vacuum drying. The polymer particles produced can then be converted into pellet form utilizing commercially available equipment.

THE POLYMER

In accordance with another embodiment of this invention a polymer produced by a specific polymerization process is provided. The polymer is characterized by having substantially only short-chain branches, particularly having little or no branches containing 8 or more carbon atoms. The polymer involved has at least 0.4 mole % branching. Of all the branches present in the polymer less than 10% are methyl branches and over 90% are even numbered alkyl branches, specifically ethyl and butyl branches. The number average molecular weight as determined by NMR techniques of this polymer is in the range of 11,000 to 30,000, preferably 15,000 to 28,000. The density of the polymer is generally in the range of about 0.920 to 0.960.

One particularly advantageous feature of the polymer made by the process described above is the substantial absence of telomers and of waxy low molecular weight components. The product made by the process contains little or no actenes, decenes or other low molecular weight olefins.

The preferred polymers of this invention are those linear polymers from ethylene as the sole olefinic polymerization feedstock which have properties within one or more of the following ranges:

| | |
| --- | --- |
| Weight Average Molecular Weight | 20,000 to 1,000,000 (or more) |
| Crystalline Melting Point | 240 to 265° F. |
| | (115 to 130° C.) |

The absence of long chain branching, i.e. the presence of only short chain branching in the polymer, is characterized by a g-value in the range of 0.9 to 1. This g-value is determined in accordance with known methods as described for instance in J. Appl. Sci. 21, 3331–3343 (1977). Attention is drawn to the fact that in the case of a polymer with broad molecular weight distribution the g-value has to be determined by fractionating the polymer, measuring the viscosities for the individual fractions, determining the g-value for the individual fractions and weight averaging the g-values found to obtain a total g-value.

The concentration of methyl branches, ethyl branches etc. is determined by standard NMR techniques as described for instance in "Carbon 13 NMR In Polymer Quantitative Analyses", by J. C. Randall and E. T. Hsieh, Chapter 9, ACS Monograph No. 247, 1983. The specific value for the mole concentration of the short chain branching is defined as the number of branch points along the polymer (CH groups) per 200 polymer backbone carbon atoms.

The molecular weights of the polymer, e.g. (weight average and number average molecular weights), are generally determined by size exclusion chromatography using commercially available equipment.

The molecular weight distribution is characterized by the heterogeneity index. This heterogeneity index (HI) is the ratio of weight average to number average molecular weight.

The density of the polymer is measured in accordance with ASTM D1505.

The crystalline melting point is measured by differential thermal analysis methods using commercially available equipment. One method for measuring the polymer melting point is described in ASTM-D1693, condition A.

Another embodiment of this invention resides in a narrowly defined class of linear, low density ethylene polymers. These polymers have ethyl and butyl branches as the predominant branching structure. The polymers are further characterized within the above given polymer parameters by those shown in the following table:

|  | Broadly | Specifically |
| --- | --- | --- |
| Density (g/cc) | <0.930 | 0.915-0.930 |
| Molecular weight (Number average) | >10,000 | 15,000-28,000 |
| HI | >10 | 15-30 |
| Long Chain Branching* | Substantially None | Not more than 1 long chain branch per 10,000 backbone carbons |

*Long chain branching determined preferably by melt flow activation energy.

The new polymers of this invention can be used in applications where other linear low density polyethylenes are used. In particular the polymers can be extruded and blown into film. The polymers can also be extruded into pipes and they can be used for injection molding, blow molding, rotational molding, wire and cable coating.

The following examples are provided to further illustrate preferred featues of this invention without undue limitation of its scope.

EXAMPLE I

Production of the Chromium Compound

The reactants, $CrCl_2$ and Grignard reagent (trimethylsilylmethylmagnesium) chloride, were obtained commercially. Reaction solvents were reagent grade, dried and distilled and stored under argon. Manipulations were carried out under Ar or $N_2$ unless indicated otherwise over an appropriate drying agent (usually calcium hydride).

Twenty five g (203 mmole) of $CrCl_2$ were suspended in 500 mL of THF at $-30°$ C. Then 250 mL of trimethylsilylmethylmagnesium chloride solution (1.6 M in diethylether, 400 mmole) was added dropwise with stirring over a two hour period while maintaining a reaction temperature of $-30°$ C. The reaction solution was then allowed to slowly warm to room temperature ($23°$ C.). The solvent was removed under vacuum and the remaining residue was extracted with five 300 mL portions of n-pentane. The combined extracts were filtered over 5 g of activated silica. The filtrate was reduced to about 300 mL by vacuum distillation and stored at $-78°$ C. overnight. The resulting brownish-black crystalline mass was recovered by decanting the mother liquor, washing the mass with 500 mL of cold ($-78°$ C.) n-pentane and drying it under vacuum, first at $-78°$ C., then gradually warming to room temperature. The yield was 35.0 g (155 mmole, 76% of theoretical) of a dark brown crystalline product analyzed as follows.

|  | C | H | Cr | Si |
| --- | --- | --- | --- | --- |
| Calculated | 42.44% | 9.79% | 22.96% | 24.81% |
| Found | 42.28% | 9.89% | 25.34% | 22.49% |

C and H were determined by elemental analysis.

Cr was determined by plasma emission analysis. Analysis is subject to greater experimental error in preparing samples than for the C, H Analyses.

Si was determined by difference.

For the purpose of X-ray diffraction analysis, suitable crystal specimens were mounted under $N_2$ in 0.3 mm Lindemann capillaries.

A. Crystal data: $C_{32}H_{88}Cr_4Si_8$, formula weight=905.73, monoclinic space group of $P2-1/n$, a=17.067(6) Å, b=13.418(4) Å, c=22.827(8) Å. (Note: The value in parenthese heres and later are estimated standard deviations). $\beta=99.85(3)$ Å, V=5153.2 Å, Z=4, $\rho=1.17$ g/cm, $\mu=10.5$ cm$^{-1}$, Mo-K$\alpha$ radiation ($\lambda=0.71073$ Å), Temperature=$-100°\pm1°$ C., F(000)=1952, and peak width at half-height=0.03°.

B Intensity measurements: Three dimensional X-ray diffraction data were collected from a single crystal (0.20×0.3× 0.35 mm) mounted on a computer-controlled Enraf-Nonius CAD4 diffractometer using Mo-K$\alpha$ radiation (graphite monochromator), $\omega$-$\theta$ scan type, a scan rate of 2°-20°/min (in omega), scan width, degrees, of 0.7+0.350 tan $\theta$, maximum $2\theta$ of 50.0°. A total of 10,057 total reflections were measured of which 9,122 were unique and which 5,635 were used in the final refinement. Corrections were Lorentz-polarization, linear decay (from 1.00 to 1.10 on I).

C. Structure solution and refinement: The computer hardware/software employed was a PDP-11/60 based Texray system utilized by Molecular Structures Corporation.

The positions of the Cr and eight Si atoms were obtained from the best E map computed with the automatic direct-methods routine in the refinement program. Refinement was determined by means of the full-matrix least-squares method. The hydrogen atoms were located from a difference map and included in the refinement with anisotropic temperature factors. The postions of 16 hydrogen atoms in the structure were obtained from isotropically refined data.

Figure 1:
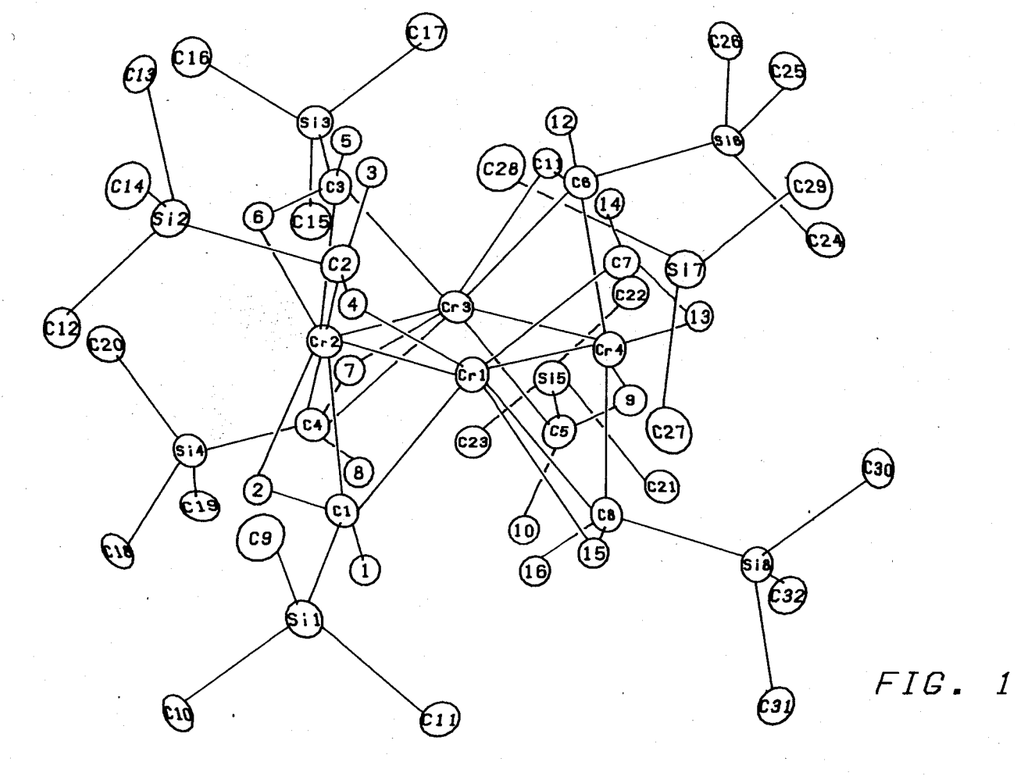
Figure 2:
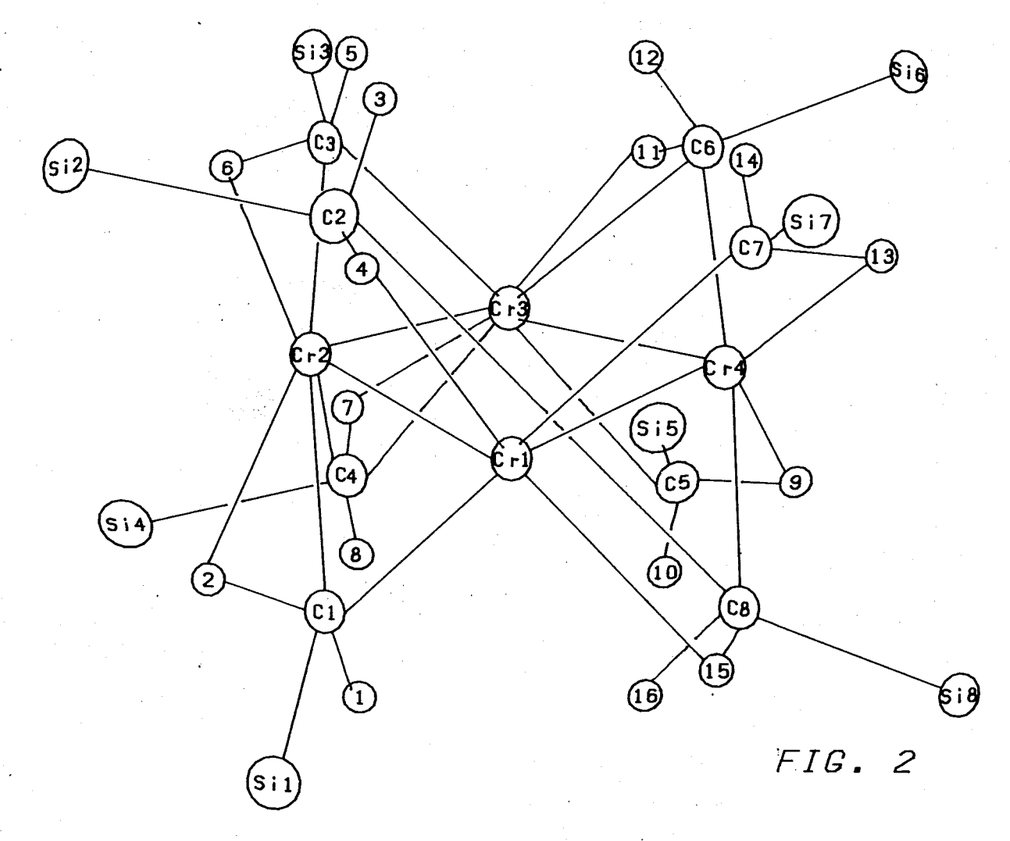
In FIG. 2 the molecule is shown yet further simplified with the all exterior methyl groups left off.

The molecular structure of $Cr_4(TMS)_8$ obtained by the above procedure and as drawn by the computer is shown in FIG. 1 with the atom-numbering scheme used and the methyl hydrogen atoms omitted for clarity. The main features are the four chromium atoms in an almost square planar configuration linked together by Cr—Cr multiple bonds and through carbon atoms to eight bridging TMS ligands. Each metal-metal bond is bridged by two TMS ligands, one below and one above the plane of the Cr atoms as is perhaps more clearly seen in FIG. 2.

Another feature of the novel compound is the bonding interactions between hydrogen atoms in the bridging positions and the chromium atoms. Each chromium atoms has two such bonding interactions represents in FIG. 2, for example, by the units H4Cr1H15, H2—Cr2—H6, H7—Cr3—H11 and H9—Cr4—H13.

Analytical results thus confirm the novel compound to be $Cr_4(TMS)_8$.

EXAMPLE II

Catalyst Preparation

Catalysts produced with $Cr_4(TMS)_8$ can be formed in situ in the reactor by injection of separately charge portions of a solution of an organochromium compound and a particulate support or by precontact of the two components before charging the resulting catalyst to the reactor. In the first method (Method A-1), the desired quantity of $Cr_4(TMS)_8$ solution as, for example, a 0.1 molar solution in n-pentane, is flushed with a portion of the diluent, e.g. isobutane, into the reactor already containing the previously charged support and remaining diluent. Ethylene is then immediately admitted and polymerization commences. No delay for catalyst reaction time is necessary. This method is also applicable to the formation of multivalent chromium catalysts (Method A-2). In Method A-2, an activated, supported hexavalent chromium-containing catalyst is separately charged to reactor where it reacts with the separately injected organochromium compound to produce the novel catalyst composition.

In Method A-1, the following supports were employed: (1) $SiO_2$; Davison Chemical Co. Grade 952 silica, surface area (SA) of about 300 m²/g and pore volume (PV) of about 1.65 cc/g, activated in a fluidized bed with dry air at 800° C. for 3 hours. (2) $Al_2O_3$; alumina, Ketjen Grade B, SA of about 300 m²/g and PV of about 1.7 cc/g, activated as above at 600° C. (3) F-$Al_2O_3$; Davison Chemical Co. high pore volume alumina, SA of about 540 m²/g and PV of about 2.0 cc/g admixed with $NH_{HF2}$ sufficient to provide a calculated 1.8 weight percent fluoride loading, the composite activated as above at 600° C. (4) F-Si-$Al_2O_3$; Davison Chemical Co. high pore volume alumina admixed with $NH_4HF_2$ and ethyl silicate 40 (partially hydrolyzed tetraethoxysilane having an equivalent 40 weight percent silia content) sufficient to provide 1.8 weight percent fluoride and a calculated 6 weight percent silica, the composite activated as above at 600° C. (5) $AlPO_4$; aluminum phosphate (P/Al atom ratio of 0.8), SA of about 350 m²/g and PV of about 1 cc/g, the composite activated as above at 400° C. or 600° C.

In Method A-2, the following activated catalysts comprising hexavalent chromium supported on silica or silica-titania were employed. The silica-supported hexavalent chromium catalyst used was Davison Chemical Co. Grade 969 MSB containing about 1 weight percent chromium, the catalyst activated as above at 800° C. The silica-titania supported hexavalent chromium catalyst used was Davison Chemical Co. Grade 963 cogel comprising about 1 weight percent chromium on a coprecipitated silica-titania cogel (about 2.5 weight percent titanium as $TiO_2$), the composite activated as above at 700° C. The preceding 963 cogel catalyst was also activated in a modified procedure wherein it was first heated for 3 hours at 800° C. in a CO atmosphere while being fluidized and then for 3 hours at 700° C. in dry air while being fluidized. This procedure is described in U.S. Pat. No. 4,151,122 and for convenience is described as R & R cogel in this invention.

A more efficient use of $Cr_4(TMS)_8$ with the support (Method B-1) or with the hexavalent chromium-containing supported catalyst (Method B-2) is accomplished by precontacting the organochromium compound with the second component in the absence of moisture and oxygen. In this method, for example, a 0.1 molar solution of $Cr_4(TMS)_8$ in n-heptane is contacted with about 1 g of second component suspended in about 20 to 30 mL of n-heptane. After several minutes of stirring, all of the organochromium compound reacts with the second component yielding a light to dark brown colored catalyst and a clear supernatant. The supernatant can be decanted and the catalyst slurry can be used as is or further washed with dry hydrocarbon and then charged to the reactor in slurry form. Alternately, the solvent can be evaporated from the catalyst slurry by gentle heating in a nitrogen or argon atmosphere. The resulting free flowing powder can be charged in that form to the reactor.

In Method B-1, a fluorided-silated alumina (described in Method A-1), number 4) was employed as the support.

In Method B-2, the supports described in Method A-2 were employed.

EXAMPLE III

Ethylene Polymerization

All polymerization runs were conducted in a 2 liter autoclave reactor under particle form (slurry conditions) containing about 600 g isobutane as diluent and a weighed amount of support or catalyst as indicated. Generally, the amount of catalyst and support employed ranged from about 0.02 to about 0.1 g. The temperature employed ranged from 85° to 105° C. (185°-221° F.). The total reactor pressure was held constant in each run at about 565 psia (3.89 Mpa) with ethylene or a combination of ethylene plus hydrogen, when used. The ethylene was supplied on demand from a pressurized reservoir as needed. A run time of 1 hour was normally employed.

Recovered polymers were stabilized with a conventional antioxidant system before physical properties were determined.

The results are given in Table I.

TABLE 1

| | Ethylene Polymerization Separate Addition of Catalytic Components to Reactor | | | | | | |
|---|---|---|---|---|---|---|---|
| | Support | | | $Cr_4(TMS)_8$ | | | |
| Run No. | Type | Activated Temp. °C. | $H_2$ psi | mmole/ g support | Calc. Prod. g/g/hr[a] | MI HLMI g/10 min | Density g/cc |
| 1 | $SiO_2$ | 400 | 0 | 0.05 | 400 | 0.07 10 | [b] |
| 2 | $SiO_2$ | 800 | 0 | 0.05 | 300 | 0.19 32 | 0.9441 |
| 3 | $AlPO_4$ | 400 | 0 | 0.05 | 1000 | 0 7.3 | 0.9532 |

TABLE 1-continued

| | Ethylene Polymerization Separate Addition of Catalytic Components to Reactor | | | | | | |
|---|---|---|---|---|---|---|---|
| | Support | | H$_2$ | Cr$_4$(TMS)$_8$ mmole/ | Calc. Prod. | MI | HLMI | Density |
| Run No. | Type | Activated Temp. °C. | psi | g support | g/g/hr$^{(a)}$ | g/10 min | | g/cc |
| 4 | AlPO$_4$ | 600 | 10 | 0.05 | 600 | 39 | large | 0.9405 |
| 5 | AlPO$_4$ | 600 | 0 | 0.15 | 2200 | 0.01 | 133 | 0.9357 |
| 6 | Al$_2$O$_3$ | 600 | 0 | 0.15 | 1500 | 0 | 0.03 | 0.9482 |
| 7 | Al$_2$O$_3$ | 600 | 10 | 0.05 | 1100 | 0.01 | 1.8 | 0.9550 |
| 8 | F—Al$_2$O$_3$ | 400 | 0 | 0.05 | 200 | — | — | — |
| 9 | F—Al$_2$O$_3$ | 500 | 0 | 0.05 | 1300 | 0 | 0.01 | — |
| 10 | F—Al$_2$O$_3$ | 600 | 0 | 0.10 | 4300 | 0 | 0.10 | 0.9484 |
| 11$^{(c)}$ | F—Al$_2$O$_3$ | 600 | 0 | 0.10 | 3800 | 0 | 0 | 0.9484 |
| 12$^{(d)}$ | F—Al$_2$O$_3$ | 600 | 0 | 0.10 | 5600 | 0 | 0.34 | 0.9488 |
| 13 | F—Si—Al$_2$O$_3$ | 600 | 0 | 0.05 | 8900 | 0 | 0.84 | 0.9504 |
| 14 | F—Si—Al$_2$O$_3$ | 600 | 10 | 0.05 | 3800 | 1.4 | 88. | 0.9591 |

Notes:
$^{(a)}$Grams polymer per g catalyst
$^{(b)}$Not determined
$^{(c)}$Run at 85° C.
$^{(d)}$Run at 103° C.
$^{(e)}$Reactor temperature of 96° C., unless indicated otherwise.

The results in Table I demonstrate that active ethylene polymerization catalyst systems result from the interaction in the reactor of the separately added Cr$_4$(TMS)$_8$ and support. The organochromium compound is most active in the presence of fluorided-alumina (Runs 10–12) and fluorided-silated alumina (Runs 13,14) with calculated productivities ranging from about 3800 to 9000 g/g catalyst/hr. The results indicate a significant improvement over pure alumina (Runs 6,7), aluminum phosphate (runs 3–5) and pure silica (Runs 1,2) in terms of productivity. The activation temperature of the support can have a marked effect on the activity of the catalyst system. For the active fluorided-alumina support, for example, an activation temperature of about 600° C. appears to be about optimum. Activities drop off sharply when activation temperatures of 400° or 500° C. are used (Runs 8,9). Increasing the reactor temperature at which the polymerization is run with a given catalyst system tends to increase catalyst activity. Runs 10, 11 and 12 indicate that raising the reactor temperature from 85° C. to 96° C. to 103° C. increases productivity from 3800 to 4300 to 5600 g/g catalyst/hr. These runs (10–12) also indicate that melt index or high load melt index does not change appreciably with reactor temperature suggesting that temperature alone is not effective in controlling polymer molecular weight with these catalyst systems.

In the presence of hydrogen, each catalyst system (excluding silica, not tested), as expected, produced lower molecular weight polymer relative to that made in the absence of hydrogen. The alumina-based systems were much less responsive to the effects of hydrogen based on the MI and/or HLMI results (MI increased from 0 to 1.4, HLMI increased from 0 to 88, Runs 6–14) than the AlPO$_4$-based system, Runs 3–5 wherein MI increased from 0 to 39, HLMI increased from 7.3 to a large undetermined value.

The polymer densities of about 0.950 g/cc obtained in the absence of hydrogen for the alumina-based systems taken in conjunction with the relatively high molecular weight polymers made as evidenced by the fractional HLMI values suggest that ethylene homopolymers were primarily made.

With the silica-based system, however, the polymer density of about 0.944 g/cc obtained in Run 2 at a MI of about 0.2 are indicative of possible branching in the polymer structure. This catalyst system is not sufficiently active to be commercially attractive.

EXAMPLE IV

Ethylene was polymerized with catalysts formed by contacting the F-Si-Al$_2$O$_3$ support with the specified organochromium compounds, isolating the solid compositions and using portions of each as before. The results are given in Table II.

TABLE II

| | Ethylene Polymerization at 95° C. Precontacted Organochromium/F—Si—Al$_2$O$_3$ Catalysts | | | | | | |
|---|---|---|---|---|---|---|---|
| Run No. | Organochromium, mmole$^{(a)}$ | | H$_2$ | Calc. Prod. | HLMI | Density | Flex. |
| | Cr(TMS)$_4$$^{(b)}$ | Cr$_4$(TMS)$_8$ | psi | g/g/hr | g/10 min | g/cc | Mod., MPa |
| 15 | 0.19 | 0 | 0 | 14,600 | 0.36 | 0.9510 | 1598 |
| 16 | 0.19 | 0 | 5 | 8800 | 14. | 0.9573 | 1078 |
| 17 | 0.19 | 0 | 50 | 2800 | 580. | 0.9629 | 1158 |
| 18 | 0 | 0.19 | 0 | 6200 | 0.39 | 0.9538 | 1180 |
| 19 | 0 | 0.19 | 50 | 3300 | 990. | 0.9656 | 1475 |

Notes:
$^{(a)}$mmoles per gram of support
$^{(b)}$Tetrakis-(trimethylsilylmethyl)chromium(IV); comparison The data in Table II show the inventive organochromium compound or a related comparison prior art organochromium compound can be prereacted with an alumina-based support to produce catalytically active compositions for ethylene polymerization. In the absence of hydrogen, the comparison catalyst (Run 10) appears to be substantially more active than the inventive catalyst based on the calculated productivity values of 14,600 vs 6200, respectively. Both catalysts produced polymers of about the same molecular weight, HLMI of about 0.36 to 0.39. The significantly lower polymer densities and flexural moduli of the polymers produced with the inventive catalyst suggest that they contain greater amounts of short chain branching, however.

EXAMPLE V

Selected polymers produced with the preceding catalysts were further evaluated with respect to molecular weight and short chain branching. The results obtained are set forth in Table III.

TABLE III

Molecular Characterization of Selected Polymers

| Support | Run No. | $M_n^{(a)}$ (× $10^3$) | $M_w^{(b)}$ (× $10^3$) | $M_z^{(b)(c)}$ (× $10^3$) | HI | Me | Et | Bu+ | Total | Et/Bu+ |
|---|---|---|---|---|---|---|---|---|---|---|
| SiO$_2$ | 2 | 19.1 | 274 | — | 14.3 | 0.26 | 0.40 | 0.29 | 0.95 | 1.4 |
| AlPO$_4$ | 5 | 14.7 | 160 | 2740 | 10.9 | 0.14 | 0.11 | 0.12 | 0.37 | 0.92 |
| F—Si—Al$_2$O$_3^{(e)}$ | 15 | 6.2 | 91 | 2020 | 14.7 | 0.10 | 0.19 | 0.19 | 0.48 | 1.0 |
| F—Si—Al$_2$O$_3^{(f)}$ | 19 | 9.5 | 209 | 2500 | 22.0 | 0.09 | 0.19 | 0.19 | 0.47 | 1.0 |

Notes:
$^{(a)}$Determined by C-13 NMR end group analysis.
$^{(b)}$Determined by size exclusion chromatography.
$^{(c)}$z-average molecular weight is the high molecular weight component.
$^{(d)}$Me is methyl, Et is ethyl, Bu+ is butyl to hexyl.
$^{(e)}$Cr compound was Cr(TMS)$_4$.
$^{(f)}$Cr compound was Cr$_4$(TSM)$_8$.

The results given in Table III demonstrate that the catalysts employed in ethylene polymerization produced polyethylenes of varying molecular weights and molecular weight distributions which contain significant amounts of short chain branches, particularly the silica-based catalyst. Gas chromatography has detected olefins of even carbon number in the liquid phase of the polymerization reactions with the catalysts. This suggests that there are several sites on the catalysts. One produces long chain polymers and another produces C$_{2n}$ olefins where n is an integer $\geq 2$. The incorporation of these olefins in the growing polymer chain could account for the observed ethyl and butyl+ branches. However, it does not account for the methyl branching since propylene is absent in the reactor liquid phase. The methyl branching apparently results from some other unknown characteristic of the polymerization mechanism.

EXAMPLE VI

Portions of the dual chromium catalyst systems enumerated in Example II, Methods A-2 and B-2, were employed in ethylene polymerization as described before. The results are presented in Tables IV and V.

sity and flexural moduli decreased and HLMI increased as the amount of injected C$_4$(TMS)$_8$ increased from zero in Run 20 to 2.52 mmole/g of hexavalent chromium catalyst in Run 23. Although not shown in the Table it was observed that induction period of about 20–55 minutes (Run 20), typically noted with hexavalent Cr catalysts, was reduced to about 5 minutes upon addition of Cr$_4$(TMS)$_8$. This suggests that the added Cr compound reduces the supported Cr$^{+6}$ center so that initiation of polymerization is not entirely dependent upon reduction of the center with ethylene alone. The variation in productivity observed ranged from 4100 in Run 20 to 7700 in Run 21 to 1420 in Run 22 also suggests that catalytic activity is increased by addition of the organochromium compound but an excess of it can depress activity.

EXAMPLE VII

Ethylene Polymerization

Prereacted Hexavalent Chromium Catalyst and Cr$_4$(TMS)$_8$

A series of ethylene polymerization runs were carried out as described in Example III wherein the designated activated supported hexavalent chromium catalyst, each containing about 1 weight percent chromium, was contacted with a solution of Cr$_4$(TMS)$_8$ as before. The 963 cogel catalyst, prior to impregnation with the solution of Cr$_4$(TMS)$_8$, was activated by heating it for 3 hours at 800° C. in carbon monoxide, cooled to 700° C. in nitrogen, then heated at 700° C. for 3 hours in dry air. It was cooled and stored in nitrogen pending further use. The 969MSB Cr catalyst component was activated

TABLE IV

Ethylene Polymerization
Separate Addition of Hexavalent Cr Catalyst and Cr$_4$(TMS)$_8$

| Run No. | Cr Cat. No. | Cr$_4$(TMS)$_8$ mmole/g | Calc. Prod. g/g/hr | MI (g/10 min) | HLMI (g/10 min) | Density g/cc | Flex.$^{(a)}$ Mod. MPa | ESCR$^{(b)}$ F$_{50}$, hrs |
|---|---|---|---|---|---|---|---|---|
| 20 | (1) | 0 | 4100 | 0 | 1.67 | 0.9577 | 1428 | — |
| 21 | (1) | 1.92 | 7700 | 0.03 | 3.11 | 0.9464 | 944 | — |
| 22 | (1) | 2.52 | 1420 | 0.05 | 5.11 | 0.9281 | 480 | — |
| 23 | (2) | 0.41 | 5200 | 0.13 | 8.06 | 0.9399 | 706 | >1000 |
| 24 | (2) | 1.32 | 4050 | 0.19 | 8.37 | 0.9372 | 642 | " |
| 25$^{(c)}$ | (2) | 0.23 | 5100 | 0.08 | 6.75 | 0.9520 | 1185 | " |
| 26$^{(c)}$ | (2) | 0.42 | 4450 | 0.22 | 12.0 | 0.9406 | 756 | " |

Notes:
(1) Davison Chemical Company grade 969 MSB catalyst, 1% Cr on microspheroidal silica, activated 3 hours in air at 800° C.
(2) Davison Chemical Company grade 963 cogel catalyst, 1% Cr on silica-titania cogel, activated 3 hours in air at 700° C., for more details see U.S. Pat. No. 4,392,990.
$^{(a)}$Flexural modulus; ASTM D790
$^{(b)}$Environmental stress cracking resistance; ASTM D1693, condition A, F$_{50}$, hours
$^{(c)}$Run with 20 psi hydrogen in reactor Runs 20–22 in Table IV demonstrate at constant reactor conditions in the absence of hydrogen in the presence of the silica-supported catalyst that polymer den- 3 hours in air at 800° C. A portion of each treated catalyst was then tested in ethylene polymerization. The results are set forth in Table V.

short chain branching amounting to about 0.85 mole percent total, a Et/Bu+ ratio of about 0.5 and a density of 0.9392 g/cc. However, with the multiple chromium

TABLE V

Ethylene Polymerization
Precontacted Cr$_4$(TMS)$_8$-Supported Cr(+6) Catalyst Compositions

| Run No. | Cr Cat. Support | Cr$_4$(TMS)$_8$ mmole/g Cat. Support | Reactor Temp. °C. | Calc. Prod. g/g/hr | Polymer MI (g/10 min) | HLMI | Density g/cc | FLex. Mod.[a] MPa | ESCR[b] F$_{50}$, hrs |
|---|---|---|---|---|---|---|---|---|---|
| 27 | 963 cogel | 0 | 95 | 3260 | 0.22 | 16 | 0.9634 | 1479 | [c] |
| 28[d] | 963 cogel | 0 | 85 | 3600 | 0.04 | 3.7 | 0.9392 | — | — |
| 29[e] | 969 MSB | 0 | 85 | 4100 | 0 | 1.7 | 0.9577 | 1428 | — |
| 30 | 952 silica[g] | 0.44 | 95 | 270 | 0.19 | 32 | 0.9441 | 678 | — |
| 31 | 963 cogel | 0.03 | 95 | 7500 | 0.21 | 13 | 0.9617 | 1417 | 69 |
| 32 | 963 cogel | 0.06 | 95 | 10800 | 0.37 | 24 | 0.9583 | 1241 | 37 |
| 33 | 963 cogel | 0.19 | 95 | 3930 | 0.60 | 35 | 0.9471 | 912 | 108 |
| 34 | 963 cogel | 0.35 | 85 | 8280 | 0.04 | 6.3 | 0.9388 | 678 | >1000 |
| 35[f] | 963 cogel | 0.35 | 95 | 6600 | 2.4 | 112 | 0.9321 | 603 | 540 |
| 36 | 963 cogel | 0.35 | 100 | 3600 | 1.5 | 112 | 0.9382 | 716 | — |
| 37 | 952 silica[g] | 0.10 | 100 | 4900 | 0.21 | 9.1 | 0.9406 | 872 | >1000 |

Notes: Runs 27-29 are controls.
[a]ASTM D790
[b]ASTM D1693, condition A
[c]A blank run signifies not determined
[d]Run with 5 ppm triethylborane (TEB), 7 g butene-1, 50 g hexene-1
[e]Run with 5 ppm TEB (triethylborane)
[f]Run with 5 psi hydrogen
[g]Davison Chemical Company The results in Table V demonstrate in invention Runs 30-37 that active ethylene polymerization catalysts can result from precontacting of activated catalysts comprising hexavalet chromium supported on silica and silica-titania. The results in Runs 31-33 show that increasing the Cr$_4$(TMS)$_8$ component from about 0.03 to 0.19 mmole/g catalyst gives a composite catalyst which yields polymers with increasing melt index (about 0.2 to 0.6), decreasing density (about 0.962 to 0.947 g/cc) at constant reactor conditions. The results in Run 34-37 indicate that increasing reactor temperature and/or the addition of hydrogen can significantly increase polymer melt index. Control run 27-29 show the results obtained with a prior art supported hexavalent chromium catalyst alone.

EXAMPLE VIII

Selected polymers shown in Tables IV and V were characterized by SEC and NMR methods to ascertain structural features. The results are presented in Table VI.

catalysts of this invention, the polymers of invention Runs 21 (density of 0.9399 g/cc), 24 (density of 0.9372 g/cc), 26 (density of 0.9406 g/cc) and 36 (density of 0.9382 g/cc), have total short chain branching ranging from about 1.02-1.60 mole % and Et/Bu+ ratios ranging from about 0.7-1. The differences are significant and demonstrate that it is possible to make medium to low density ethylene polymers (linear low density polyethylene) by employing ethylene as the sole monomer with the catalyst systems of this invention.

EXAMPLE IX

A series of ethylene polymerization runs was made as before at 95° C. using catalysts formed as before by contacting an activated catalyst comprising hexavalent chromium (about 1 weight percent chromium based on the catalyst weight) supported on the silica-titania cogel previously described with the specified organochromium compound. the chromium compounds employed were: (a) dicyclopentadienylchromium, abbreviated Cr(CP)$_2$; (b) dicumenechromium(O), abbreviated

TABLE VI

Molecular Characterization of Selected Polymers (Tables IV, V)

| Run No. | Supported Hex. Cr Cat. | M$_w$(SEC) (× 10$^{-3}$) | M$_n$(NMR) (× 10$^{-3}$) | HI | Density g/cc | Mole % Bunching Me | Et | Bu+ | Total | Et/Bu+ |
|---|---|---|---|---|---|---|---|---|---|---|
| 21 | 969 MSB | 248 | 8.48 | 29 | 0.9399 | 0 | 0.56 | 0.50 | 1.06 | 1.12 |
| 24 | 963 cogel | 281 | 6.79 | 41 | 0.9372 | 0.06 | 0.80 | 0.74 | 1.60 | 1.08 |
| 25 | 963 cogel | 281 | 10.8 | 26 | 0.9520 | 0 | 0.13 | 0.13 | 0.26 | 1.00 |
| 26 | 963 cogel | 239 | 8.37 | 29 | 0.9406 | 0 | 0.58 | 0.53 | 1.11 | 1.09 |
| 28[a] | 963 cogel | 341 | 6.06 | 56 | 0.9392 | 0 | 0.29 | 0.56 | 0.85 | 0.52 |
| 29[b] | 969 MSB | 313 | 7.50 | 42 | 0.9577 | 0 | 0 | 0 | 0 | — |
| 30 | 952 silica | 274 | 1.56 | 175 | 0.9441 | 0.22 | 0.44 | 0.19 | 0.85 | 2.32 |
| 36 | 963 cogel | 103 | 7.86 | 13 | 0.9382 | 0 | 0.64 | 0.86 | 1.50 | 0.74 |
| 37 | 952 silica | 174 | 7.37 | 24 | 0.9340 | 0.05 | 0.87 | 0.75 | 1.67 | 1.16 |

[a]Control ethylene/1-butene/1-hexene terpolymer made only with a hexavalent Cr/silica-titania prior art catalyst
[b]Control ethylene homopolymer made only with a prior art hexavalent Cr/silica catalyst The properties of the polymers shown in Table VI are typical of those made with the indicated catalyst systems. The linear high density polyethylene of Run 29 is shown to be essentially free of short chain branching as expected. The terpolymer of Run 28 shows some Cr(CUM)$_2$ and cited in McDaniel, U.S. Pat. No. 4,369,295; bis(2,4-dimethylpentadienyl)chromium(II), abbreviated Cr(DMPD)$_2$; and Cr(TMS)$_4$ and $Cr_4(TMS)_8$, both described in this application. The results are given in Table VII.

TABLE VII

Ethylene Polymerization Precontacted Hexavalent Chromium Catalyst and Organochromium Compound

| Run No. | Organochromium Compound Type | mmole/g catalyst | Calculated Product g/g/hr | HLMI g/10 min. | Density g/cc |
|---|---|---|---|---|---|
| 38 | $Cr(CP)_2$ | 0.20 | 1 | — | — |
| 39 | $Cr(CUM)_2$ | 0.20 | 6400 | 10 | 0.9529 |
| 40 | $Cr(DMPD)_2$ | 0.20 | 10900 | 18 | 0.9616 |
| 41[a] | $Cr(TMS)_4$ | 0.30 | 8800 | 6.1 | 0.9562 |
| 42 | $Cr_4(TMS)_8$ | 0.19 | 3900 | 35 | 0.9471 |

[a]Run at 100° C. to increase polymer MI into the range of the others.

The results in Table VII indicate that the type of organochromium compound employed in the precontacting of the activated, supported hexavalent catalyst has a significant effect on catalyst activity as well as on the physical properties of the resulting polymers. Based on equivalents of organochromium added, comparison Run 38 shows that $Cr(CP)_2$ yielded a dead catalyst. The compound $Cr_4(TMS)_8$, invention Run 42, was the most effective in lowering polymer density suggesting that significant short chain branching is present as verified in earlier examples. The other organochromium compounds, in order of effectiveness in lowering polymer density are $Cr(CUM)_2$, $Cr(TMS)_4$ and $Cr(DMPD)_2$, in coparison Runs 39, 41, 40, respectively.

EXAMPLE X

A series of ethylene polymerization runs was made as before at 100° C. using catalysts formed by contacting the previously described activated hexavalent chromium/silica-titania catalyst with either $Cr(CUM)_2$ or $Cr_4(TMS)_8$ and isolating the catalyst compositions. At the conclusion of each run, the reactor liquid phase was sampled by gas chromatography to determine the presence of ethylene oligomers. The column could not separate butenes from the isobutane diluent employed in the reactor, hence values for 1-butene are missing. Higher olefins are of greater concern, however, due to the greater probability of being odor, smoking and sticky problems in processing. Polymerization time in run 43 was 12 minutes, in run 44 was 11 minutes, in run 45 was 15 minutes and in run 46 was 60 minutes. The results obtained are given in Table VIII.

TABLE VIII

Higher Olefin Content of Reactor Liquid

| Run No. | Organochromium Compound Type | mmole/g catalyst | Polymer Density g/hr | $C_6^=$ | $C_8^=$ | $C_{10}^=$ | $C_{12}^=+$ |
|---|---|---|---|---|---|---|---|
| 43 | $Cr(CUM)_2$ | 0.3 | 0.945 | 0.97 | 0.31 | 0.27 | 0.13 |
| 44 | $Cr_4(TMS)_8$ | 0.3 | 0.939 | 0.52 | 0.10 | — | — |
| 45 | $Cr_4(TMS)_8$ | 0.3 | 0.952 | 0.16 | 0.03 | — | — |
| 46 | $Cr_4(TMS)_8$ | 0.3 | 0.958 | 0.04 | 0.01 | — | — |

The results set forth in Table VIII demonstrate that the invention composite catalyst of Runs 44-46 produce only small amounts of $C_6^-$ and $C_8^-$ olefins, the absolute quantities of which increase with decreasing polymer density. However, in the production of polymer of about the same density, the control catalyst of Run 43 produced about 6 times the amount of $C_6^-$ olefins and about 10 times the amount of $C_8^-$ as did the invention catalyst of Run 45. The control catalyst also produced significant amounts of $C_{10}^-$, $C_{12}^-$ and higher olefins whereas none were detected with invention catalyst.

EXAMPLE XI

Ethylene as the sole monomer was polymerized in a stirred 2 liter reactor in the gas phase with a dual valence chromium catalyst. The catalyst was prepared under the usual dry, oxygen-free conditions by impregnating a previously activated 963 cogel catalyst (see Example VII) containing about 1 weight percent hexavalent chromium with sufficient $Cr_4(TMS)_8$ dissolved in n-pentane to provide 0.2 mg atom of added divalent Cr per gram of cogel catalyst. This corresponds to about 1 weight percent added divalent Cr as $Cr_4(TMS)_8$ based on the weight of cogel catalyst plus Cr compound. Following impregnation, the solvent was removed by heating the mixture under a nitrogen stream to dryness at about 50°-60° C. The dual valence chromium catalyst was stored under nitrogen.

Polymerization was conducted in the 2 liter stirred reactor by purging it with nitrogen, heating it to near the desired temperature, charging the catalyst and pressuring the reactor to the specified level with ethylene. As before, ethylene was supplied on demand from a pressurized reservoir during each 1 hour run. The reactor temperature was somewhat difficult to control under the conditions employed.

The reactor temperatures, pressures and resulting polymer properties are shown in Table IX.

TABLE IX

Ethylene Polymerization, Gas Phase

| Run No. | 47 | 48 | 49 |
|---|---|---|---|
| Reactor Conditions | | | |
| Temperature (°F.) | 190 to 196 | 207 to 237 | 203 to 239 |
| Pressure (psia) | 215 | 315 | 315 |
| Polymer Properties | | | |
| Density (g/cc) | 0.9510 | 0.9480 | 0.9460 |
| MI (g/10 min) | 0.28 | 1.5 | 2.9 |
| HLMI (g/10 min) | 22.6 | 65.3 | 126 |
| Flex. Modulus (MPa) | 1079 | 1049 | 965 |
| Branching Structures | | | |
| Total Branching (mole %) | 0.42 | 0.76 | 1.00 |
| Isolated Branches (mole %) | 0.40 | 0.71 | 0.92 |
| Clustered Branches (mole %) | 0.02 | 0.05 | 0.08 |
| Branch Distribution (Normalized against total branching) | | | |
| Ethyl Branches | 0.315 | 0.279 | 0.225 |
| Butyl Branches | 0.465 | 0.576 | 0.631 |
| Hexyl and longer branches | 0.220 | 0.145 | 0.144 |
| Branch Dispersity | | | |
| Observed (%) | 97.2 | 96.2 | 96.0 |
| Random (%) | 99.6 | 99.2 | 99.0 |
| Relative (%) | 97.6 | 97.0 | 97.0 |
| Saturated/Vinyl End Group Ratio | 1.061 | 1.209 | 1.403 |

The microstructure of the polymer has been obtained by NMR methods. The above example shows that the catalyst described can be utilized not only in the liquid phase but also in the gas phase to produce polymers from ethylene having, however, a significant amount of short branches of even carbon number.

Resonable variations and modifications which will become apparent to those skilled in the art can be made in this invention without departing from the spirit and scope thereof.

What is claimed is:

1. Polymerization process comprising contacting at least one-mono-1-olefin having 2–8 carbon atoms per molecule with a catalyst comprising a solid inorganic oxide support and a chromium compound having the formula $$Cr_n(R)_{2n}$$

wherein
n is an integer of 3 or more,
R is a ligand having the formula $$-CH_2-MR^1R^2R^3$$

wherein
M is C, Si, Ge, Sn or Pb,
$R^1$, $R^2$, $R^3$, which can be the same or different, are hydrocarbyl substituents consisting of carbon and hydrogen atoms
under polymerization conditions to produce a reaction mixture containing an olefin polymer and
recovering said olefin polymer from said reaction mixture.

2. A method according to claim 1 wherein said support contains in addition activated catalytic hexavalent chromium sites.

3. A process according to claim 2 wherein said chromium compound is octakis(μ-trimethylsilylmethyl)tetrachromium(II).

4. A process according to claim 1 wherein said chromium compound is octakis(μ-trimethylsilylmethyl)tetrachromium(II).

5. A method according to claim 4 wherein said support comprises silica.

6. A process according to claim 1 wherein said solid inorganic oxide support comprises silica.

7. A method according to claim 6 wherein said support is co-precipitated silica/titania.

8. A method according to claim 1 wherein said support comprises alumina.

9. A method according to claim 1 wherein said support is a fluorided silica alumina.

10. A method according to claim 9 wherein said chromium compound is octakis(μ-trimethylsilylmethyl)tetrachromium(II).

11. A method according to claim 10 wherein said support contains in addition activated catalytic hexavalent chromium sites.

12. A method according to claim 11 wherein said mono-1-olefin is ethylene, said ethylene being the sole olefin.

13. A method according to claim 1 wherein said olefin is ethylene, said ethylene being the sole olefin.

14. A method according to claim 1 wherein said catalyst is contacted with said olefin in the liquid phase employing a liquid diluent.

15. A method according to claim 14 wherein said diluent is removed from the polymer and the polymer recovered without further purification steps.

16. A method according to claim 1 wherein said olefin is contacted in the gas phase with said catalyst.

17. A method according to claim 1 wherein said polymer produced is substantially dry and non-sticky.

18. Polymerization process comprising contacting ethylene as the sole monomer in a liquid diluent with a catalyst comprising a solid inorganic oxide support and a chromium compound having the formula $$Cr_n(R)_{2n}$$

wherein
n is an integer of 3 or more,
R is a ligand having the formula $$-CH_2-MR^1R^2R^3$$

wherein
M is C, Si, Ge, Sn or Pb,
$R^1$, $R^2$, $R^3$, which can be the same or different, are hydrocarbyl substituents consisting of carbon and hydrogen atoms
under polymerization conditions to produce a reaction mixture containing an olefin polymer, and
recovering a reactor product comprising diluent and linear ethylene polymer, said reactor product being essentially free of $C_{10}$ and $C_{12}$ olefins.

19. A method according to claim 18 wherein said chromium compound is octakis(μ-trimethylsilylmethyl)tetrachromium(II).

* * * * *